(12) United States Patent
Kisenwether et al.

(10) Patent No.: US 8,841,235 B2
(45) Date of Patent: Sep. 23, 2014

(54) AGRICULTURAL PESTICIDE COMPOSITIONS

(75) Inventors: Michael J. Kisenwether, Bensalem, PA (US); Michelle McKnight, Philadelphia, PA (US); Krishnamurthy Shanmuganandamurthy, Plainsboro, NJ (US); Valerio Bramati, Milan (IT); Thierry Sclapari, Skillman, NJ (US)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/136,734

(22) Filed: Aug. 9, 2011

(65) Prior Publication Data

US 2012/0040833 A1 Feb. 16, 2012

Related U.S. Application Data

(60) Provisional application No. 61/401,242, filed on Aug. 10, 2010.

(51) Int. Cl.
*A01N 57/00* (2006.01)
*A01N 25/02* (2006.01)
*A01N 25/30* (2006.01)

(52) U.S. Cl.
CPC ............... *A01N 25/30* (2013.01); *A01N 25/02* (2013.01)
USPC ........................................ 504/127; 504/128

(58) Field of Classification Search
None
See application file for complete search history.

(56) References Cited

U.S. PATENT DOCUMENTS

| | | | |
|---|---|---|---|
| 3,225,074 A | 12/1965 | Cowen et al. |
| 3,527,593 A | 9/1970 | Bland et al. |
| 3,723,357 A | 3/1973 | Hansen |
| 3,882,051 A | 5/1975 | Hansen |
| 4,011,388 A | 3/1977 | Murphy et al. |
| 4,107,328 A | 8/1978 | Michaels |
| 4,117,107 A | 9/1978 | Shapiro |
| 4,122,159 A | 10/1978 | Madrange et al. |
| 4,137,191 A | 1/1979 | Lohr |
| 4,243,549 A | 1/1981 | Messenger et al. |
| 4,452,732 A | 6/1984 | Bolich, Jr. |
| 4,477,365 A | 10/1984 | Verboom et al. |
| 4,585,846 A | 4/1986 | Schulz et al. |
| 4,607,076 A | 8/1986 | Schulz et al. |
| 4,650,848 A | 3/1987 | Schulz et al. |
| 4,703,797 A | 11/1987 | Djabbarah |
| 4,708,998 A | 11/1987 | Schulz et al. |
| 4,742,135 A | 5/1988 | Schulz et al. |
| 4,788,247 A | 11/1988 | Schulz et al. |
| 4,822,847 A | 4/1989 | Schulz et al. |
| 4,831,092 A | 5/1989 | Bock et al. |
| 4,835,234 A | 5/1989 | Valint et al. |
| 4,882,405 A | 11/1989 | Schulz et al. |
| 4,996,045 A | 2/1991 | Leighton et al. |
| 5,153,289 A | 10/1992 | Schulz et al. |
| 5,164,120 A | 11/1992 | Borland et al. |
| 5,180,414 A | 1/1993 | Darchy et al. |
| 5,258,358 A | 11/1993 | Kocur et al. |
| 5,292,942 A | 3/1994 | Aigner et al. |
| 5,338,793 A | 8/1994 | Loftin |
| 5,341,932 A | 8/1994 | Chen et al. |
| 5,354,906 A | 10/1994 | Weitmeyer et al. |
| 5,385,206 A | 1/1995 | Thomas |
| 5,439,317 A | 8/1995 | Bishop et al. |
| 5,464,806 A | 11/1995 | Kassebaum et al. |
| 5,551,516 A | 9/1996 | Norman et al. |
| 5,580,856 A | 12/1996 | Prestrelski et al. |
| 5,612,285 A | 3/1997 | Arnold |
| 5,686,400 A | 11/1997 | Urfer et al. |
| 5,700,760 A | 12/1997 | Magin et al. |
| 5,703,016 A | 12/1997 | Magin et al. |
| 5,747,416 A | 5/1998 | McArdle et al. |
| 5,863,863 A | 1/1999 | Hasebe et al. |
| 5,874,394 A | 2/1999 | Thomas et al. |
| 5,877,143 A | 3/1999 | Abbas et al. |
| 5,888,934 A | 3/1999 | Townson et al. |
| 5,897,699 A | 4/1999 | Chatterji et al. |

(Continued)

FOREIGN PATENT DOCUMENTS

| | | |
|---|---|---|
| CA | 2554335 | 8/2005 |
| EP | 0373851 | 6/1990 |

(Continued)

OTHER PUBLICATIONS

Ullmann's Encyclopedia of Industrial Chemistry, 5th Ed., vol. A 10, Edited by Gerhartz et al., pp. 176-177, Wiley-VCH Verlag GmbH & Co. KGaA, Weinheim, Germany, May 5, 1994.

"Application Guide for Household & Industrial Markets"; McIntyre Group Ltd., Copyright 2002, (Jan. 2003), obtained online @ http://www.dewolfchem.com/pdf/Mcintyre_HI&I_Application_Guide.pdf, (downloaded Mar. 6, 2012).

(Continued)

*Primary Examiner* — Alton Pryor

(57) ABSTRACT

A pesticide composition contains, based on 100 parts by weight ("pbw") of the composition: (a) from about 15 to about 65 pbw of one or more pesticide compounds, (b) from greater than 0 to about 10 pbw of one or more fatty acid ($C_1$-$C_3$) esters, and (c) optionally, up to about 20 pbw of one or more surfactants, wherein the surfactant component typically comprises: (i) one or more betaine surfactants, (ii) one or more glycoside surfactants, (iii) one or more amine oxide surfactants, (iv) one or more fatty (ether) amine alkoxylate surfactants, or (v) a surfactant mixture comprising at least one surfactant from each of at least two of the surfactant categories (i), (ii), (iii), and (iv). A method for controlling a target pest, includes the steps of diluting the above described pesticide composition with a diluent comprising water and applying the diluted pesticide composition to the target pest and/or to the environment of the target pest.

18 Claims, No Drawings

(56) References Cited

U.S. PATENT DOCUMENTS

| | | | |
|---|---|---|---|
| 5,912,209 A | 6/1999 | Kassebaum et al. |
| 5,985,798 A | 11/1999 | Crudden |
| 5,998,332 A | 12/1999 | Sato et al. |
| 6,030,928 A | 2/2000 | Stahl et al. |
| 6,036,638 A | 3/2000 | Nwawka |
| 6,127,318 A | 10/2000 | Sato et al. |
| 6,165,939 A | 12/2000 | Agbaje et al. |
| 6,210,476 B1 | 4/2001 | Chatterji et al. |
| 6,284,854 B1 | 9/2001 | Bowers et al. |
| 6,288,010 B1 | 9/2001 | Rose et al. |
| 6,302,209 B1 | 10/2001 | Thompson et al. |
| 6,329,322 B1 | 12/2001 | Reierson |
| 6,346,588 B1 | 2/2002 | Fench et al. |
| 6,369,122 B1 | 4/2002 | Subramanyam |
| 6,376,566 B1 | 4/2002 | Bergeron et al. |
| 6,407,042 B1 * | 6/2002 | Ward et al. ............ 504/358 |
| 6,417,268 B1 | 7/2002 | Zhang et al. |
| 6,432,878 B1 | 8/2002 | Brigance |
| 6,432,884 B1 | 8/2002 | Lachut |
| 6,451,731 B1 | 9/2002 | Agbaje et al. |
| 6,500,784 B1 | 12/2002 | Mille et al. |
| 6,566,408 B1 | 5/2003 | Cotrell et al. |
| 6,642,178 B2 | 11/2003 | Woznica et al. |
| 6,645,912 B1 | 11/2003 | Mille et al. |
| 6,645,914 B1 | 11/2003 | Woznica et al. |
| 6,653,257 B2 | 11/2003 | Mille et al. |
| 6,770,268 B1 | 8/2004 | Hall et al. |
| 6,770,594 B2 | 8/2004 | Bickers et al. |
| 6,831,108 B2 | 12/2004 | Dahanayake et al. |
| 6,881,707 B2 | 4/2005 | Howat et al. |
| 6,992,046 B2 | 1/2006 | Bramati et al. |
| 7,135,437 B2 | 11/2006 | Pallas et al. |
| 7,316,990 B2 * | 1/2008 | Tank et al. ............ 504/206 |
| 8,236,730 B2 * | 8/2012 | Bramati et al. ............ 504/206 |
| 8,263,529 B2 | 9/2012 | Suzuki et al. |
| 8,383,137 B2 | 2/2013 | Modaressi et al. |
| 2002/0187917 A1 | 12/2002 | Lazarowitz |
| 2003/0118540 A1 | 6/2003 | Charlton et al. |
| 2004/0097372 A1 | 5/2004 | Abraham et al. |
| 2004/0110644 A1 | 6/2004 | Halliday et al. |
| 2004/0121917 A1 | 6/2004 | Pakulski |
| 2005/0003965 A1 | 1/2005 | Xiao et al. |
| 2005/0010009 A1 | 1/2005 | Schulz et al. |
| 2005/0020454 A1 | 1/2005 | Francini et al. |
| 2005/0130842 A1 | 6/2005 | Fleute-Schlachter |
| 2005/0170965 A1 | 8/2005 | Bramati et al. |
| 2006/0019830 A1 | 1/2006 | Xu et al. |
| 2006/0060354 A1 | 3/2006 | Lewis et al. |
| 2007/0155628 A1 | 7/2007 | Pazhianur et al. |
| 2007/0282075 A1 | 12/2007 | Koch et al. |
| 2008/0103047 A1 | 5/2008 | Gioia et al. |
| 2008/0312083 A1 | 12/2008 | Gioia et al. |
| 2009/0018018 A1 | 1/2009 | Gioia et al. |
| 2010/0069269 A1 | 3/2010 | Prat et al. |
| 2010/0093874 A1 | 4/2010 | Monin et al. |
| 2010/0140531 A1 | 6/2010 | Prat et al. |
| 2011/0009269 A1 | 1/2011 | Gioia et al. |
| 2011/0015071 A1 | 1/2011 | Kisenwether et al. |
| 2012/0165195 A1 | 6/2012 | Iskandar et al. |

FOREIGN PATENT DOCUMENTS

| | | |
|---|---|---|
| EP | 0274369 | 9/1990 |
| EP | 0483095 | 10/1991 |
| EP | 0370338 | 5/1992 |
| EP | 0508022 | 10/1992 |
| EP | 0573118 | 12/1993 |
| EP | 0449159 | 7/1995 |
| EP | 0810239 | 9/2000 |
| JP | 11-349826 | 6/1998 |
| JP | 10183176 | 7/1998 |
| WO | 9212637 | 8/1992 |
| WO | 92/14907 | 9/1992 |
| WO | 9701281 | 1/1997 |
| WO | 9706230 | 2/1997 |
| WO | 97/36489 | 10/1997 |
| WO | 98/14060 | 4/1998 |
| WO | 99/03895 | 1/1999 |
| WO | 99/15610 | 4/1999 |
| WO | 9945780 | 9/1999 |
| WO | 99/62338 | 12/1999 |
| WO | 0038523 | 7/2000 |
| WO | 0067571 | 11/2000 |
| WO | 0067573 | 11/2000 |
| WO | 0108482 | 2/2001 |
| WO | 0117358 | 3/2001 |
| WO | 0126463 | 4/2001 |
| WO | 0126469 | 4/2001 |
| WO | 0189302 | 11/2001 |
| WO | 02/26036 | 4/2002 |
| WO | 03/049813 | 6/2003 |
| WO | 2004/107861 | 12/2004 |
| WO | 2004107862 | 12/2004 |
| WO | 2007003112 | 1/2007 |

OTHER PUBLICATIONS

Basheva et al.; Role of Betaine as Foam Booster in the Presence of Silicone Oil Drops; Langmuir 2000, 16, 1000-1013; Received Jun. 16, 1999; 2000 American Chemical Society Published on Web Dec. 8, 1999.

* cited by examiner

AGRICULTURAL PESTICIDE COMPOSITIONS

FIELD OF THE INVENTION

This invention relates to agricultural pesticide compositions.

BACKGROUND OF THE INVENTION

Many agricultural pesticides, including insecticides, fungicides, herbicides, miticides, and plant growth regulators, are applied in the form of a liquid composition. In addition to the pesticide, such liquid compositions typically include one or more adjuvant compounds intended to improve one or more properties of the liquid composition, such as for example, storage stability, ease of handling, and/or pesticide efficacy against target organisms.

An approach that has been found to be convenient in some cases is to provide an easily transportable concentrated pesticide composition that comprises a relatively high concentrations of pesticide compound and adjuvant compounds that is diluted at the point of use to provide a pesticide composition for application to target pests. However, in some cases, such as those in which the relatively high concentrations of pesticide and adjuvant compounds results in a concentrated pesticide composition that is non-homogeneous, unstable, and/or difficult to handle, for example, due to intractably high viscosity, this approach may not be feasible and/or convenient.

There is a continuing interest in concentrated pesticide compositions that exhibit improved stability and handling properties and can be readily diluted with water to form efficacious aqueous pesticide compositions that may be spray applied to target pests.

SUMMARY OF THE INVENTION

In a first aspect, the present invention is directed to a pesticide composition, more typically an aqueous pesticide composition, comprising, based on 100 parts by weight ("pbw") of the composition:
(a) from about 15 to about 65 pbw of one or more pesticide compounds,
(b) from greater than 0 to about 10 pbw of one or more fatty acid ($C_1$-$C_3$) esters, and
(c) optionally, up to about 20 pbw of one or more surfactants.

The pesticide composition of the present invention is a pesticide concentrate composition that contains a high load of pesticide and that unexpectedly exhibits good stability, low viscosity, and improved ease of handling.

In a second aspect, the present invention is directed to a method for making the above described pesticide composition of the present invention, comprising mixing the above described components the pesticide composition to form the pesticide composition.

In a third aspect, the present invention is directed to a method for controlling a target pest, comprising diluting the above described pesticide composition with an aqueous diluent and applying the diluted pesticide composition to the target pest and/or to the environment of the target pest.

DETAILED DESCRIPTION OF INVENTION AND PREFERRED EMBODIMENTS

As used herein, the term "alkyl" means a saturated straight chain or branched chain hydrocarbon radical, such as for example, methyl, ethyl, n-propyl, iso-propyl, n-butyl, sec-butyl, t-butyl, pentyl, n-hexyl.

As used herein, the term "alkoxyl" means an oxy group substituted with an alkyl group, such as, for example, methoxyl, ethyoxyl, propoxyl.

As used herein, the term "cycloalkyl" means a saturated cyclic hydrocarbon radical, such as, for example, cyclopentyl, cyclohexyl.

As used herein, the term "hydroxyalkyl" means a saturated straight chain or branched chain hydrocarbon radical substituted one or more carbon atoms with a hydroxyl group, such as for example, hydroxymethy, hydroxyethyl, hydroxypropyl.

As used herein, the term "alkenyl" means an unsaturated straight chain, branched chain, or cyclic hydrocarbon radical that contains one or more carbon-carbon double bonds, such as, for example, ethenyl, 1-propenyl, and 2-propenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl, and tristyrylphenyl.

As used herein, the term "aralkyl" means an alkyl group substituted with one or more aryl groups, such as, for example, phenylmethyl, phenylethyl, and triphenylmethyl.

As used herein, the term "alkylamido" means amido radical, substituted with an alkyl group, such as dodecylamido, tetradecylamido.

As used herein, the term "alkylamidoalkyl" means an alkyl group substituted with an alkylamido group, such as dodecylamidoalkyl, tetradecylamidoalkyl.

As used herein, the terminology "($C_m$-$C_n$)" in reference to an organic group, wherein m and n are each integers, indicates that the group may contain from m carbon atoms to n carbon atoms per group.

As used herein, the term "agronomically acceptable salts" refers to salts prepared from agronomically acceptable non-toxic bases or acids including inorganic or organic bases and inorganic or organic acids. Typical agronomically acceptable salts the compound referred to herein comprise an anion derived from the compound, for example, by deprotonation of a hydroxy or hydroxyalkyl substituent, and one or more positively charged counterions. Suitable positively charged counterions include inorganic cations and organic cations, such as for example, sodium cations, potassium cations, calcium cations, magnesium cations, isopropylamine cations, ammonium cations, and tetraalkylammonium cations.

References herein to saccharide compounds and moieties, such as, for example, glycosides, polyglycosides, and residues thereof, include, unless otherwise explicitly limited, all linear and cyclized forms of the saccharide compound or moiety, as well as isomers thereof.

As used herein, the term "aqueous" in reference to a composition means that the composition comprises greater than 0 pbw water per 100 pbw of the composition.

As referred to herein, the "weight" a given material is typically given on the basis of the named material. For example, a reference to 25 parts by weight of a given surfactant, wherein the surfactant compound is provided as a 50% by weight aqueous solution of the surfactant compound, would typically mean 25 parts by weight of the surfactant compound itself, which would correspond to 50 parts by weight of the 50 wt % aqueous solution of the surfactant compound.

As used herein, the terminology "pesticide spray mix composition" means a pesticide composition that contains pesticide in amount effective to control a target pest, such as, for example, a target plant, fungus, bacterium, or insect, when the pesticide composition is spray applied to the pest and/or to the environment of the pest at a given application rate and the terminology "pesticide concentrate composition" means a composition that contains a relatively high concentration of pesticide that is suitable to be diluted with water to form a pesticide spray mix composition.

As used herein, the terminology "effective amount" in reference to the relative amount of a pesticide in a pesticide composition means the relative amount of pesticide that is effective to control a target pest, for example, a target plant, fungus, bacterium, or insect, when the pesticide composition is applied to the pest and/or to the environment of the pest at a given application rate and the terminology "herbicidally effective amount" in reference to the relative amount of herbicide in an herbicidal composition means the relative amount that is effective to control growth of a target plant when the herbicidal composition is spray applied to the target plant and/or to the environment of the plant at a given application rate.

Suitable pesticides are biologically active compounds used to control agricultural pests and include, for example, herbicides, plant growth regulators, crop dessicants, fungicides, bacteriocides, bacteriostats, insecticides, and insect repellants, as well as their water soluble salts and esters. Suitable pesticides include, for example, triazine herbicides such as metribuzin, hexaxinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; phenoxyacetic acids such as 2,4-D; diphenyl ether herbicides such as fluazifop, acifluorfen, bifenox, or oxyfluorfen; dinitro aniline herbicides such as trifluralin; organophosphonate herbicides such as glufosinate salts and esters and glyphosate salts and esters; dihalobenzonitrile herbicides such as bromoxynil, or ioxynil, benzoic acid herbicides such as dicamba, dipyridilium herbicides such as paraquat. Suitable fungicides include, for example, nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chlorinated aromatic fungicides such as chloroneb; dichloro aniline fungicides such as iprodione, strobilurin fungicides such as kresoxim-methyl, trifloxystrobin or azoxystrobin; chlorothalonil; copper salt fungicides such as copper oxychloride; sulfur; phenylamides; and acylamino fungicides such as metalaxyl or mefenoxam. Suitable insecticides, include, for example, carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoide insecticides such as thiamethoxam or imidacloprid; pyrethroid insecticides such as lambda-cyhalothrin, cypermethrin or bifenthrin, and oxadiazine insecticides such as indoxacarb, imidachlopryd, or fipronil. Suitable miticides include, for example, propynyl sulfite miticides such as propargite; triazapentadiene miticides such as amitraz; chlorinated aromatic miticides such as chlorobenzilate, or tetradifan; and dinitrophenol miticides such as binapacryl. Suitable nematicides include carbamate nematicides, such as oxamyl.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources.

In one embodiment, the pesticide comprises one or more compounds selected from herbicides, plant growth regulators, crop dessicants, fungicides, bacteriocides, bacteriostats, insecticides, miticides, nematocides, insect repellants, and mixtures thereof.

In one embodiment, the pesticide is an herbicide and the pesticide composition is an herbicide composition.

In one embodiment, the pesticide comprises one or more herbicide compounds selected from glyphosate, glufosinate, dicamba, 2,4-D, their respective water soluble salts and esters, and mixtures thereof.

In one embodiment, the herbicide composition comprises one or more herbicide compounds selected from glyphosate, water soluble glyphosate salts, water soluble glyphosate esters, and mixtures thereof, more typically selected from the sodium salt of glyphosate, the potassium salt of glyphosate, the ammonium salt of glyphosate, the dimethylamine salt of glyphosate, the isopropyl amine salt of glyphosate, the trimesyl salt of glyphosate, and mixtures thereof.

In one embodiment, the pesticide composition of the present invention comprises, based on 100 pbw of the pesticide composition, from about 15 pbw, more typically from about 30 pbw, and even more typically from about 40 pbw, to about 65 pbw, more typically about 60 pbw, and even more typically about 55 pbw, of the one or more pesticide compounds.

In one embodiment, the fatty acid $(C_1-C_3)$alkyl ester component of the pesticide composition of the present invention comprises one or more compounds according to structure (I):

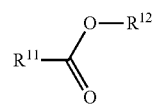

wherein:
$R^{11}$ is $(C_6-C_{24})$alkyl or $(C_6-C_{24})$alkenyl, and
$R^{12}$ is $(C_1-C_3)$alkyl, more typically, methyl.

In one embodiment, the fatty acid $(C_1-C_3)$alkyl ester comprises one or more compounds according to structure (I) wherein $R^{11}$ is $(C_6-C_{24})$alkyl, such as, for example, hexyl, heptyl, octyl, nonyl, decyl, undecyl, dodecyl, tridecyl, tetradecyl, pentadecyl, hexadecyl, heptadecyl, octadecyl, nonadecyl, eicosyl, docosyl, tricosyl, tetracosyl.

In one embodiment, the fatty acid $(C_1-C_3)$alkyl ester comprises one or more compounds according to structure (I) wherein $R^{11}$ is mono-unsaturated or poly-unsaturated $(C_6-C_{24})$alkenyl, such as, for example, cis-9-hexadecenyl all cis-7,10,13-hexadecatrienyl, cis-6-octadecenyl, trans-6-octadecenyl, cis-7-octadecenyl, cis-9-octadecenyl, trans-9-octadecenyl, cis-11-octadecenyl trans-11-octadecenyl, cis-12-octadecenyl, cis, cis-9,12-octadecedienyl, trans-9,12-octadecedienyl, all cis-6,9,12-octadecatrienyl, all cis-9,12, 15-octadecatrienyl, all cis-6,9,12,15,-octadecatetraenyl, cis-11-eicosenyl, cis, cis-11,14-eicosadienyl, all cis-11,14,17-eicosatrienyl all cis-5,8,11,14-eicosatetraenyl, all cis-8,11, 14,17-eicosatetraenyl, all cis-5,8,11,14,17-eicosapentaenyl, cis-13-docosenyl, cis, cis-13,16-docosadienyl, all cis-6,9,12-octadecatrienyl, all cis-7,10,13,16-docosatetraenyl, all cis-7,10,13,16,19-docosapentaenyl, all cis-4,7,10,13,16,19-docosahexaenyl, cis-15-tetracosenyl, all cis-9,12,15,18,21-tetracosapentaenyl, or all cis-6,9,12,15,18,21-tetracosahexaenyl.

In one embodiment, the fatty acid $(C_1-C_3)$alkyl ester comprises one or more compounds according to structure (I) wherein $R^{11}$ is $(C_6-C_{24})$alkyl and one or more compounds according to structure (I) wherein $R^{11}$ is mono-unsaturated or poly-unsaturated $(C_6-C_{24})$alkenyl.

In one embodiment, the fatty acid $(C_1-C_3)$alkyl ester comprises one or more compounds according to structure (I) wherein $R^{11}$ is $(C_6-C_{24})$alkyl and one or more compounds according to structure (I) wherein $R^{11}$ is mono-unsaturated or poly-unsaturated $(C_6-C_{24})$alkenyl, and $R^{12}$ is methyl.

In one embodiment, the fatty acid $(C_1-C_3)$alkyl ester comprises one or more compounds according to structure (I) wherein $R^{11}$ is $(C_6-C_{12})$alkyl or $(C_6-C_{12})$alkenyl. In another embodiment, the fatty acid ester comprises one or more compounds according to structure (I) wherein $R^{11}$ is $(C_{13}-C_{24})$alkyl or $(C_{13}-C_{24})$alkenyl.

In one embodiment, the fatty acid $(C_1-C_3)$alkyl ester comprises one or more compounds according to structure (I) wherein $R^{11}$ is $(C_6-C_{12})$alkyl or $(C_6-C_{12})$alkenyl, and $R^{12}$ is methyl. In another embodiment, the fatty acid ester comprises one or more compounds according to structure (I) wherein $R^{11}$ is $(C_{13}-C_{24})$alkyl or $(C_{13}-C_{24})$alkenyl, and $R^{12}$ is methyl.

Suitable fatty acid $(C_1-C_3)$alkyl esters may be made by, for example, acid-catalyzed esterification of corresponding fatty acids or corresponding fatty mono-, di- and/or tri-glycerides with a $(C_1-C_3)$ alcohol, more typically methanol, or by transesterification of the corresponding fatty mono-, di- and/or tri-glycerides with a $(C_1-C_3)$ alcohol, more typically methanol. Convenient sources of fatty acids and fatty acid glycerides include vegetable oils, such as, for example, palm oil, soybean oil, rapeseed oil, high erucic acid rapeseed oil, sunflower seed oil, peanut oil, cottonseed oil, palm kernel oil, linseed oil, coconut oil, olive oil, safflower oil, sesame oil, canola oil and animals fats, such as tallow, lard oil or fish oil, as well as mixtures of such compounds. Suitable fatty acid methyl esters are commercially available. One commercial source of fatty acid $(C_1-C_3)$alkyl esters is "bio-diesel" fuels made by transesterification of vegetable oils or animal fats with a $(C_1-C_3)$ alcohol, more typically methanol.

In one embodiment, the fatty acid $(C_1-C_3)$alkyl ester component of the composition of the present invention comprises one or more of methyl, ethyl, or propyl hexanoate, methyl, ethyl, or propyl heptanoate, methyl, ethyl, or propyl octanoate, methyl, ethyl, or propyl nonanoate, methyl, ethyl, or propyl decanoate, methyl, ethyl, or propyl undecanoate, methyl, ethyl, or propyl dodecanoate, methyl, ethyl, or propyl tridecanoate, methyl, ethyl, or propyl tetradecanoate, methyl, ethyl, or propyl pentadecanoate, methyl, ethyl, or propyl hexadecanoate, methyl, ethyl, or propyl heptadecanoate, methyl, ethyl, or propyl octadecanoate, methyl, ethyl, or propyl nonadecanoate, methyl, ethyl, or propyl eicosanoate, methyl, ethyl, or propyl docosanoate, methyl, ethyl, or propyl tricosanoate, methyl, ethyl, or propyl tetracosanoate, methyl, ethyl, or propyl cis-9-hexadecenoate, methyl, ethyl, or propyl all cis-7,10,13-hexadecatrienoate methyl, ethyl, or propyl cis-6-octadecenoate, methyl, ethyl, or propyl trans-6-octadecenoate, methyl, ethyl, or propyl cis-7-octadecenoate, methyl, ethyl, or propyl cis-9-octadecenoate, methyl, ethyl, or propyl trans-9-octadecenoate, methyl, ethyl, or propyl cis-11-octadecenoate, methyl, ethyl, or propyl trans-11-octadecenoate, methyl, ethyl, or propyl cis-12-octadecenoate, methyl, ethyl, or propyl cis, cis-9,12-octadecedienoate, methyl, ethyl, or propyl trans-9,12-octadecedienoate, methyl, ethyl, or propyl all cis-6,9,12-octadecatrienoate, methyl, ethyl, or propyl ester all cis-9,12,15-octadecatrienoate, methyl, ethyl, or propyl all cis-6,9,12,15,-octadecatetraenoate, methyl, ethyl, or propyl cis-11-eicosenoate, methyl, ethyl, or propyl cis, cis-11,14-eicosadienoate, methyl, ethyl, or propyl all cis-11,14,17-eicosatrienoate, methyl, ethyl, or propyl all cis-5,8,11,14-eicosatetraenoate, methyl, ethyl, or propyl all cis-8,11,14,17-eicosatetraenoate, methyl, ethyl, or propyl all cis-5,8,11,14,17-eicosapentaenoate, methyl, ethyl, or propyl cis-13-docosenoate, methyl, ethyl, or propyl cis, cis-13,16-docosadienoate, methyl, ethyl, or propyl all cis-6,9,12-octadecatrienoate, methyl, ethyl, or propyl all cis-7,10,13,16-docosatetraenoate, methyl, ethyl, or propyl all cis-7,10,13,16,19-docosapentaenoate, methyl, ethyl, or propyl all cis-4,7,10,13,16,19-docosahexaenoate, methyl, ethyl, or propyl cis-15-tetracosenoate methyl, ethyl, or propyl all cis-9,12,15,18,21-tetracosapentaenoate, methyl, ethyl, or propyl all cis-6,9,12,15,18,21-tetracosahexaenoate, including mixtures two or more of any of such fatty acid $(C_1-C_3)$alkyl esters. More typically, the fatty acid ester component of the composition of the present invention comprises a mixture of two or more of such fatty acid $(C_1-C_3)$alkyl esters, in the form of one or more $(C_1-C_3)$alkyl esters of one or more vegetable oils, more typically, a methylated vegetable oil, even more typically, methylated soybean oil or methylated rapeseed oil.

In one embodiment, the pesticide composition of the present invention comprises, based on 100 pbw of the pesticide composition, from greater than 0 pbw, more typically from about 0.001 pbw and even more typically from about 0.005 pbw, to about 10 pbw, more typically about 8 pbw, and even more typically about 6 pbw, of the one or more fatty acid $(C_1-C_3)$ alkyl esters.

In one embodiment, the surfactant component of the pesticide composition of the present invention comprises:
(i) one or more betaine surfactants,
(ii) one or more glycoside surfactants,
(iii) one or more amine oxide surfactants,
(iv) one or more fatty (ether) amine alkoxylate surfactants, or
(v) a surfactant mixture comprising at least one surfactant from each of at least two of the surfactant categories (i), (ii), (iii), and (iv).

In one embodiment, wherein the surfactant component of the pesticide composition comprises one or more glycoside surfactants, the pesticide composition comprises, based on 100 pbw of the pesticide composition, less than 4 pbw, more typically less than 1 pbw, and even more typically, 0 pbw, of any lipophilic emulsifier, such as, for example, fatty acid polyol partial esters, fatty alcohols and fatty alcohol polyethers, or a mixture thereof.

Betaine surfactants suitable as the betaine surfactant component of the pesticide composition of the present invention are known compounds and include, for example, N-alkyl derivatives of glycine and N-alkyl derivatives of 13-alanine, more typically N-alkyl derivatives of dimethyl glycine. In one embodiment, the betaine surfactant component of the respective adjuvant composition or pesticide composition of the present invention comprises one or more compounds according to formula (II):

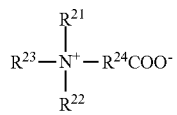

wherein:
$R^{21}$ and $R^{22}$ are each independently alkyl, alkenyl, alkoxyalkyl, hydroxyalkyl, hydroxy-terminated poly(oxyalkylene), or alkoxy-terminated poly(oxyalkylene),
$R^{23}$ is a hydrophobic moiety, and
$R^{24}$ is methylene or dimethylene.

In one embodiment, $R^{21}$ and $R^{22}$ are each independently $(C_1\text{-}C_6)$alkyl, $(C_1\text{-}C_6)$alkenyl, an alkoxyalkyl group having from 2 to 6 carbon atoms per group, hydroxy$(C_1\text{-}C_6)$alkyl, or $R^{25}\text{---}(OC_xH_{2x})_y\text{---}$, wherein $R^{25}$ is H or $(C_1\text{-}C_6)$alkyl, x is, independently for each $\text{---}(OC_xH_{2x})\text{---}$ unit, 2 or 3, and y is an integer of from 1 to 20, more typically from 1 to 10. In one embodiment, at least one of $R^{21}$ and $R^{22}$ is $R^{25}\text{---}(OC_xH_{2x})_y\text{---}$ that contains $\text{---}(OC_xH_{2x})\text{---}$ units in which x is 2, that is, oxyethylene units, and $\text{---}(OC_xH_{2x})\text{---}$ units in which x is 3, that is, oxypropylene units, wherein the oxyethylene units and oxypropylene units are arranged in random order or in blocks.

In one embodiment, $R^{23}$ is an alkyl, alkenyl, alkoxyalkyl, alkylaminoalkyl, alkylamidoalkyl, alkenylaminoalkyl, or alkenylamidoalkyl group, each typically having from 6 to 30 carbon atoms per group, wherein the alkyl moiety of the respective alkoxyalkyl, alkylaminoalkyl, and alkylamidoalkyl groups may optionally be substituted with one or more hydroxyl groups, and wherein the alkoxyalkyl group may optionally be linked to the nitrogen atom of structure (I) via a divalent oxyalkylene radical of from 1 to 6 oxy$(C_2\text{-}C_3)$ alkylene units.

In one embodiment:
$R^{21}$ and $R^{22}$ are each independently $(C_1\text{-}C_3)$alkyl,
$R^{23}$ is $(C_6\text{-}C_{30})$alkyl, alkoxyalkyl having from 6 to 30 carbon atoms per group, $(C_6\text{-}C_{24})$alkylamido$(C_1\text{-}C_6)$alkyl, or $(C_6\text{-}C_{24})$alkenylamido$(C_1\text{-}C_6)$alkyl, and
$R^{24}$ is methylene or dimethylene.

In one embodiment, $R^{21}$ and $R^{22}$ are each independently $(C_1\text{-}C_6)$alkyl, more typically methyl, $R^{23}$ is $(C_6\text{-}C_{30})$alkyl, more typically $(C_8\text{-}C_{22})$alkyl, more typically $(C_8\text{-}C_{18})$alkyl, and still more typically, $(C_{12}\text{-}C_{14})$alkyl, and $R^{24}$ is methylene.

In one embodiment $R^{21}$ and $R^{22}$ are each independently $(C_1\text{-}C_6)$alkyl, more typically methyl, $R^{23}$ is alkylamidoalkyl, more typically $(C_6\text{-}C_{24})$alkylamido$(C_1\text{-}C_6)$alkyl, and, even more typically, $(C_8\text{-}C_{20})$alkylamidopropyl, and $R^{24}$ is methylene.

Suitable betaines surfactants include, for example, decyl dimethyl betaine, undecyl dimethyl betaine, dodecyl dimethyl betaine, tridecyl dimethyl betaine, tetradecyl dimethyl betaine, coco dimethyl betaine, $(C_{12}\text{-}C_{14})$alkyl dimethyl betaine, hexadecyl dimethyl betaine, heptadecyl dimethyl betaine, octadecyl dimethyl betaine, dodecylamidopropyl dimethyl betaine, cocoamidopropyl dimethyl betaine, oleylamidopropyl betaine, lauryl dihydroxypropylglycinate, lauryl di(hydroxy-poly(ethoxy))glycinate, β-alanine, cocodimethylbetaine, and mixtures thereof.

In one embodiment, the composition comprises a betaine surfactant component, wherein the betaine surfactant component comprises a mixture of one or more betaine surfactant compounds and one or more polyhydric alcohol compounds, more typically, glycerine, and wherein the ratio of the amount, by weight, of the one or more betaine surfactant compounds to the amount, by weight, of the one or more polyhydric alcohol compounds ranges from 0.1:1 to 1:0.1, more typically from 0.5: to 1:0.5.

Glycoside surfactants suitable as the glycoside surfactant component of the pesticide composition of the present invention are generally known compounds, which characteristically comprise a sugar moiety bound to a hydrophobic moiety. Suitable sugar moieties include monosaccharide moieties and polysaccharide moieties. Suitable hydrophobic moieties include hydrocarbyl moieties, more typically $(C_4\text{-}C_{30})$hydrocarbyl moieties, even more typically $(C_4\text{-}C_{30})$alkyl groups. In one embodiment, the glycoside surfactant component of the present invention is selected from alkylmonoglycoside surfactants, alkylpolyglycoside surfactants, and mixtures thereof.

In one embodiment, the glycoside surfactant component of the respective adjuvant composition or pesticide composition of the present invention comprises one or more compounds according to formula (III):

wherein:
$R^{31}$ is a hydrophobic moiety,
each $R^{32}$ is independently a divalent monosaccharide radical,
$R^{33}$ is a monovalent monosaccharide radical, and m is an integer of from 0 to about 10, more typically from 0 to 4, even more typically from 0 to 2.

In one embodiment, $R^{31}$ is hydrocarbyl, substituted hydrocarbyl. More typically, $R^{31}$ is a linear or branched saturated or unsaturated aliphatic group or an aromatic group, more typically, alkyl, cycloalkyl, aryl, or aralkyl, and even more typically, alkyl.

In one embodiment, $R^{31}$ contains from 4 to 30 carbon atoms, more typically from 6 to 24 carbon atoms and even more typically from 8 to 22 carbon atoms.

In one embodiment, $R^{31}$ is $(C_4\text{-}C_{22})$alkyl. In another embodiment, $R^{31}$ is $(C_4\text{-}C_8)$alkyl. In another embodiment, $R^4$ is $(C_8\text{-}C_{14})$alkyl. In another embodiment, $R^{31}$ is $(C_{14}\text{-}C_{22})$alkyl.

As used herein in reference to a monosaccharide radical, the term "divalent" means that the radical is a linking group that links two other moieties via a respective single covalent bond between the divalent monosaccharide radical and each of the two other moieties and corresponds to a monosaccharide residue formed by, for example, conceptually removing two hydrogen atoms from a molecule of the monosaccharide. In one embodiment, each $R^{32}$ is a divalent radical selected from divalent pentose radicals and divalent hexose radicals. Suitable divalent pentose radicals and divalent hexose radicals include divalent radicals of aldopentoses, aldohexoses, ketopentoses, and ketohexoses, such as, for example, divalent radicals of ribose, arabinose, xylose, lyxose, allose, altrose, glucose, mannose, gulose, idose, galactose, talose, dihydroxyacetone, erthrulose, psicose, fructose, sorbose, and tagatose.

In one embodiment, each $R^{32}$ is independently a divalent radical of ribose, arabinose, xylose, lyxose, allose, altrose, glucose, mannose, gulose, idose, galactose, talose, dihydroxyacetone, erthrulose, psicose, fructose, sorbose, or tagatose.

In one embodiment, each $R^{32}$ is independently a divalent radical of glucose, arabinose, or xylose, more typically, glucose.

As used herein in reference to a monosaccharide radical, the term "monovalent" means that the radical is a an end group that caps one other moiety via a single covalent bond to the one other moiety and corresponds to a monosaccharide residue formed by, for example, conceptually removing one hydrogen atom from a molecule of the monosaccharide. In one embodiment, $R^{33}$ is a monovalent radical selected from monovalent pentose radicals and monovalent hexose radicals. Suitable monovalent pentose radicals and monovalent hexose radicals include divalent radicals of ribose, arabinose, xylose, lyxose, allose, altrose, glucose, mannose, gulose, idose, galactose, talose, dihydroxyacetone, erthrulose, psicose, fructose, sorbose, and tagatose.

In one embodiment, $R^{33}$ is monovalent radical of ribose, arabinose, xylose, lyxose, allose, altrose, glucose, mannose, gulose, idose, galactose, talose, dihydroxyacetone, erthrulose, psicose, fructose, sorbose, or tagatose.

In one embodiment, $R^{33}$ is a monovalent radical of glucose, arabinose, or xylose, more typically, glucose.

When m=0, glycoside surfactant according to structure (III) is a monoglycoside surfactant. When m is greater than 0, the glycoside surfactant according to structure (III) is a polyglycoside surfactant.

In one embodiment, m is an integer greater than 0, $-(R^{32})_m R^{33}$ is a monovalent moiety consisting of a chain of m polymerized monomeric saccharide units $R^{32}$ with a terminal saccharide group $R^{33}$.

In one embodiment, each $R^{32}$ radical and the $R^{33}$ radical is a residue of the same saccharide compound. In one embodiment, each $R^{32}$ and $R^{33}$ is a glucose residue.

In one embodiment, each $R^{32}$ and $R^{33}$ group is independently selected from monosaccharide residues, and include residues of at least two different monosaccharides. In one embodiment, each $R^{32}$ and $R^{33}$ is independently selected from glucose residues, arabinose residues, and xylose residues, more typically, from arabinose residues and xylose residues, and include residues of at least two different monosaccharides.

In one embodiment, the glycoside surfactant according to formula (III) is a species according to formula (III-a):

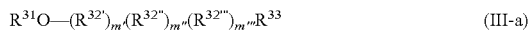

(III-a)

wherein:
$R^{31}$ and $R^{33}$ are each described as above,
each $R^{32'}$, $R^{32''}$, and $R^{32'''}$ is an $R^{32}$ group, wherein $R^{32'} \neq R^{32''} \neq R^{32'''}$, each m', m'', and m''' is an integer of from 0 to 10, wherein m'+m''+m'''=m, and
the sequence of the $R^{32'}$, $R^{32''}$, and $R^{32'''}$ units in the $-(R^{32'})_{m'}(R^{32''})_{m''}(R^{32'''})_{m'''}-$ chain is a random, alternating, or a block sequence, more typically, a random sequence.

In one embodiment, the glycoside surfactant is a mixture of monoglycosides, wherein the average value of m for the combined glycosides of the mixture is 1.

In one embodiment, the glycoside surfactant is a mixture of one or more monoglycoside and one or more polyglycoside, or a mixture of polyglucosides, wherein the average value of m for the combined glycosides of the mixture is greater than 1, typically greater than or equal to 1.1, more typically greater than or equal to 1.2 and even more typically greater than or equal to 1.3. In one embodiment, the average value of m is less than or equal to 8, more typically less than or equal to 4 and even more typically less than or equal to 2.

In one embodiment, the glycoside surfactant comprises one or more glycoside surfactants according to structure (III), wherein R is alkyl, cycloalkyl, aryl, alkaryl, aralkyl, alkenyl, alkoxy, or aryloxy, more typically ($C_8$-$C_{22}$)alkyl, each $R^5$ and $R^6$ is independently a hexose residue, more typically a glucose residue, even more typically a D-glucose residue, and m is an integer of from 0 to 5, more typically 0 to 2.

In one embodiment, the glycoside surfactant comprises one or more glycoside surfactants according to structure (III), wherein: $R^{31}$ is alkyl, cycloalkyl, aryl, alkaryl, aralkyl, alkenyl, alkoxy, or aryloxy, more typically ($C_8$-$C_{22}$)alkyl, each $R^{32}$ and $R^{33}$ is independently a pentose residue, more typically arabinose residue or a xylose residue, even more typically, an L-arabinose residue or a D-xylose residue, and m is an integer of from 0 to 5, more typically 0 to 2.

Suitable glycoside surfactants include for example, ($C_4$-$C_{22}$)alkylhexosides, such as butylglucoside, octylglucoside, nonylglucoside, decylglucoside, undecylglucoside, dodecylglucoside, hexadecylglucoside, octadecylglucoside, erucylpolyglucoside, and mixtures thereof, ($C_4$-$C_{22}$)alkylpolyhexosides, such as butylpolyglucosides, octylpolyglucosides, nonylpolyglucosides, decylpolyglucosides, undecylpolyglucosides, dodecylpolyglucosides, tetradecylpolyglucosides, hexadecylpolyglucosides, octadecylpolyglucosides, erucylpolyglucosides, and mixtures thereof, ($C_4$-$C_{22}$)alkylpentosides, such as octylarabinoside, nonylarabinosides, decylarabinoside, dodecylarabinoside, hexadecylarabinoside, erucylarabinoside, octylxyloside, nonylxyloside, decylxyloside, dodecylxyloside, hexadecylxyloside, erucylxyloside and mixtures thereof, and ($C_4$-$C_{22}$)alkylpolypentosides, such as butylpolyarabinosides, octylpolyarabinosides, nonylpolyarabinosides, decylpolyarabinosides, undecylpolyarabinosides, dodecylpolyarabinosides, tetradecylpolyarabinosides, hexadecylpolyarabinosides, octadecylpolyarabinosides, erucylpolyarabinosides, butylpolyxylosides, octylpolyxylosides, nonylpolyxylosides, decylpolyxylosides, undecylpolyxylosides, dodecylpolyxylosides, tetradecylpolyxylosides, hexadecylpolyxylosides, octadecylpolyxylosides, and erucylpolyxylosides butylpoly(arabino-co-xylo)sides, octylpoly(arabino-co-xylo)sides, nonylpoly(arabino-co-xylo)sides, decylpoly(arabino-co-xylo)sides, undecylpoly(arabino-co-xylo)sides, dodecylpoly(arabino-co-xylo)sides, tetradecylpoly(arabino-co-xylo)sides, hexadecylpoly(arabino-co-xylo)sides, octadecylpoly(arabino-co-xylo)sides, erucylpoly(arabino-co-xylo)sides, and mixtures thereof, wherein the terminology "poly(arbino-co-xylo)side" denotes a copolymeric chain of monomeric residues of arabinose and xylose.

Amine oxide surfactants suitable as the amine oxide surfactant component of the present invention are generally known compounds. In one embodiment, the amine oxide surfactant component of the respective adjuvant composition or pesticide composition of the present invention comprises one or more compounds according to structure (IV):

(IV)

wherein each of $R^{41}$, $R^{42}$, and $R^{43}$ is independently an organic group, which may, optionally, include one or more heteroatoms, typically each independently selected from O, N, and P heteroatoms.

In one embodiment, the amine oxide component of the composition of the present invention comprises at least one compound according to formula (IV), wherein $R^{41}$, $R^{42}$, and $R^{43}$ are each independently alkyl, hydroxyalkyl, alkoxyl, alkenyl, $R^{44}$—$R^{45}$—, $R^{46}$—C(O)—NH—$R^{47}$—, a phosphate moiety, a phosphonate moiety, or any two of $R^{41}$, $R^{42}$, and $R^{43}$ are fused to form a 5- to 8-membered saturated or unsaturated heterocyclic ring that includes the nitrogen atom of the amine oxide and, optionally, further includes a second nitrogen atom or an oxygen atom as a ring member, and which may be further substituted with alkyl or amino on one or more of the ring atoms, $R^{44}$ and $R^{46}$ are each independently H, alkyl, or alkenyl, $R^{45}$ is alkyleneoxy or polyalkyleneoxy, more typically poly (ethyleneoxy), poly(propyleneoxy), and $R^{47}$ is alkylene, polyalkylene, alkyleneoxy, or polyalkyleneoxy.

In one embodiment, $R^{41}$, $R^{42}$, and $R^{43}$ are each independently ($C_1$-$C_{30}$)alkyl, ($C_1$-$C_{30}$)hydroxyalkyl, ($C_1$-$C_{30}$) alkoxyl, ($C_2$-$C_{30}$)alkenyl, $R^{44}$—$R^{45}$—, $R^{46}$—C(O)—NH—$R^{47}$—, a phosphate moiety, a phosphonate moiety, or any two of $R^7$, $R^8$, and $R^9$ are fused to form a 5- or 6-membered saturated or unsaturated heterocyclic ring that includes the nitrogen atom of the amine oxide and, optionally, further includes a second nitrogen atom or an oxygen atom as a ring member and which may be further substituted with ($C_1$-$C_{30}$) alkyl or amino on one or more of the ring atoms, $R^{44}$ and $R^{46}$ are each independently H, ($C_1$-$C_{30}$)alkyl, or ($C_2$-$C_{30}$)alkenyl, $R^{45}$ is —($C_pH_{2p}$)$_q$—, wherein p is, independently for each —($C_pH_{2p}$)— unit, 2, 3, or 4, and q is an integer of from 1 to 50, and $R^{47}$ is methylene, ($C_2$-$C_{30}$)polymethylene, or —(OC$_r$H$_{2r}$)$_s$— wherein r is, independently for each —(OC$_r$H$_{2r}$)— unit, 2, 3, or 4, and s is an integer of from 1 to 50.

In one embodiment, at least one of $R^{41}$, $R^{42}$, and $R^{43}$ is ($C_1$-$C_{30}$)alkyl, ($C_1$-$C_{30}$)hydroxyalkyl, ($C_1$-$C_{30}$)alkoxyl, or ($C_2$-$C_{30}$)alkenyl. In one embodiment, one of $R^{41}$, $R^{42}$, and $R^{43}$ is ($C_8$-$C_{30}$)alkyl or ($C_8$-$C_{30}$)alkenyl, more typically ($C_8$-$C_{18}$)alkyl, and the other two of $R^{41}$, $R^{42}$, and $R^{43}$ are each independently ($C_1$-$C_7$)alkyl, ($C_1$-$C_7$)hydroxyalkyl, ($C_1$-$C_7$) alkoxyl.

In one embodiment, at least one of $R^{41}$, $R^{42}$, and $R^{43}$ is $R^{46}$—C(O)—NH—$R^{47}$—, wherein $R^{46}$ is ($C_1$-$C_{30}$)alkyl or ($C_2$-$C_{30}$)alkenyl, and $R^{47}$ is ($C_1$-$C_{20}$)alkylene, more typically methylene or ($C_2$-$C_{20}$)polymethylene.

In one embodiment, at least one of $R^{41}$, $R^{42}$, and $R^{43}$ is a phosphate moiety or a phosphonate moiety.

In one embodiment, two of $R^{41}$, $R^{42}$, and $R^{43}$ are fused to form a 5- or 6-membered saturated or unsaturated heterocyclic ring which includes the nitrogen atom of the amine oxide and a second nitrogen atom as ring members and wherein the ring is substituted with amino on one or more of the ring atoms.

In one embodiment, two of $R^{41}$, $R^{42}$, and $R^{43}$ are fused to form a 5- or 6-membered saturated or unsaturated heterocyclic ring which includes the nitrogen atom of the amine oxide and an oxygen atom as ring members and wherein the ring is substituted with alkyl on one or more of the ring carbons.

Suitable amine oxides include, for example, behenamine oxide (N,N-dimethyl-1-docosanamine-N-oxide), cocamidopropylamine oxide (N-[3-(dimethylamino)propyl]coco amides-N-oxide), coco-morpholine oxide (morphaline, 4-coco alkyl derivs, 4-oxides), decylamine oxide (N,N-dimethyl-1-decylamine-N-oxide), decyltetradecylamine oxide, diaminopyrimidine oxide, dihydroxyethyl $C_8$-$C_{10}$)alkoxypropylamine oxide, dihydroxyethyl ($C_9$-$C_{11}$)alkoxypropylamine oxide, dihydroxyethyl ($C_{12}$-$C_{15}$)alkoxypropylamine oxide, dihydroxyethyl cocamine oxide (N,N-bis(2-hydroxyethyl) cocamine oxide), dihydroxyethyl lauramine oxide (N,N-bis(2-hydroxyethyl) lauramine oxide), dihydroxyethyl stearamine oxide (N,N-bis(2-hydroxyethyl) stearamine oxide), dihydroxyethyl tallowamine oxide (N,N-bis(2-hydroxyethyl) tallowamine oxide), hydrogenated palm kernel amine oxide, hydrogentated tallowamine oxide, hydroxyethyl hydroxypropyl ($C_{12}$-$C_{15}$) alkoxypropylamine oxide, isostearamidopropylamine oxide (N-[3-(dimethylamino) propyl]isooctadecanamide-N-oxide), isostearamidopropyl morpholine oxide (N-[3-(4-morpholinyl)propyl]isooctadecanamide-N-oxide), lauramidopropylamine oxide (N-[3-(dimethylamino)propyl]dodecanamide-N-oxide), lauramine oxide (N,N-dimethyl-1-dodecanamine-N-oxide), methyl morpholine oxide, myristamidopropylamine oxide (N-[3-(dimethylamino)propyl]tetradecanamide-N-oxide), myristamine oxide (N,N-dimethyl-1-tetradecanamine-N-oxide), myristyl/cetyl amine oxide (N,N-dimethyl-1-myristamine/cetylamine-N-oxide), oleamidopropylamine oxide (N-[3-(dimethylamino)propyl]-9-octadecenamide-N-oxide), oleamine oxide (N,N-dimethyl-9-octadecen-1-Amine-N-oxide), olivamidopropylamine oxide, palmitamidopropylamine oxide, palmitamine oxide, PEG-3 lauramine oxide, potassium dihydroxyethyl cocamine oxide phosphate, potassium trisphosphonomethylamine oxide, sesamidopropylamine oxide, ($C_{12}$-$C_{14}$)alkyldimethyl amine oxides, soyamidopropylamine oxide, stearamidopropylamine oxide, stearamine oxide, tallowamidopropylamine oxide, tallowamine oxide, undecylenamidopropylamine oxide, wheat germamidopropylamine oxide, as well as mixtures of such amine oxides.

Fatty (ether) amine alkoxylate surfactants suitable as the fatty (ether) amine alkoxylate surfactant component of the present invention are generally known compounds. In one embodiment, the fatty (ether) amine alkoxylate surfactant component of the respective adjuvant composition or pesticide composition of the present invention comprises one or more compounds according to structure (V):

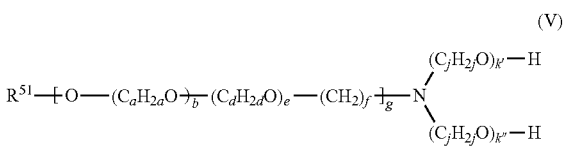

wherein:

$R^{51}$ is ($C_8$-$C_{22}$)alkyl or ($C_8$-$C_{22}$)alkenyl, a, b, d, e, f, g, j, k' and k" are each integers, wherein:

a, d, f, and j are each independently 2, 3, or 4, b and e are each independently from 0 to 5, g is 0 or 1, k' and k" are each from 0 to 20 and the sum of t'+t" is from 1 to 40, more typically from 2 to 40, and even more typically from 5 to 30.

In one embodiment, the fatty (ether) amine alkoxylate surfactant component comprises one or more compounds according to structure (V) wherein $R^{51}$ is ($C_{12}$-$C_{24}$)alkyl, such as lauryl (ether) amine alkoxylates, coco (ether) amine alkoxylates, stearyl (ether) amine alkoxylates, octadecyl (ether) amine alkoxylates, and hydrogenated tallow (ether) amine alkoxylates, and mixtures thereof.

In one embodiment, the fatty (ether) amine alkoxylate component comprises one or more compounds according to structure (V) wherein $R^{51}$ is mono-unsaturated ($C_{12}$-$C_{24}$)alkenyl or poly-unsaturated $(C_{12}-C_{24})$alkenyl, such as oleyl (ether) amine alkoxylates and mixtures thereof.

In one embodiment, the fatty (ether) amine alkoxylate component comprises one or more compounds according to structure (V) wherein $R^{51}$ is $(C_{12}-C_{24})$alkyl and one or more compounds according to structure (V) wherein $R^{51}$ is mono-unsaturated $(C_{12}-C_{24})$alkenyl or poly-unsaturated $(C_{12}-C_{24})$alkenyl, such as tallow (ether) amine alkoxylates and mixtures thereof.

In one embodiment, a is 2 or 3, b is from 1 to 5, c is 2 or 3, d is from 1 to 5, a is not equal to b, and g is 1.

In one embodiment, a is 2 or 3, b is from 1 to 5 d is 0, and g is 1.

In one embodiment, g is 0 and the fatty (ether) amine alkoxylate is a fatty amine alkoxylate.

In one embodiment, j is 2.

In one embodiment, $R^{51}$ is $(C_8-C_{22})$alkyl or $(C_8-C_{22})$alkenyl, g is 0, j is 2, and k' and k" are each from 0 to 20 and the sum of t'+t" is from 1 to 40, more typically from 2 to 40, and even more typically from 5 to 30 and the fatty (ether) amine alkoxylate of structure (V) is a fatty amine ethoxylate, such as, for example, a lauryl amine ethoxylate, coco amine ethoxylate, stearyl amine ethoxylate, octadecyl amine ethoxylate, hydrogenated tallow amine ethoxylate, oleyl amine ethoxylate, tallow amine ethoxylate, or a mixture thereof.

In one embodiment, the fatty (ether) amine alkoxylate comprises a tallow amine ethoxylate having an average of from about 5 to about 30 ethyleneoxy units per molecule In one embodiment, the pesticide composition of the present invention comprises, based on 100 pbw of the pesticide composition, from greater than 0 pbw, more typically from about 0.5 pbw and even more typically from about 1 pbw, to about 20 pbw, more typically about 10 pbw, and even more typically about 8 pbw, of the one or more surfactants.

The pesticide composition of the present invention may optionally further comprise other surfactants, which may be one or more anionic, cationic, nonionic, amphoteric, or zwitterionic surfactant, in addition to the above described surfactants (i), (ii), (ii), (iv), or (v). In one embodiment, the amount of such additional surfactants is limited and the surfactant component of the respective adjuvant or pesticide composition consists of:
(i) one or more betaine surfactants,
(ii) one or more glycoside surfactants,
(iii) one or more amine oxide surfactants,
(iv) one or more fatty (ether) amine alkoxylate surfactants, or
(v) a surfactant mixture comprising at least one surfactant from each of at least two of the surfactant categories (i), (ii), (iii), and (iv), and
(vi) further comprising, based on 100 pbw of the selected surfactant or surfactant mixture (i), (ii), (iii), (iv), or (v), from 0 to about 10 pbw, more typically from 0 to about 5 pbw, and even more typically from 0 to less than about 1 pbw, of one or more anionic, cationic, nonionic, amphoteric, or zwitterionic surfactant other than the selected surfactant or surfactant mixture (i), (ii), (iii), (iv) or (vi).

In one embodiment, the pesticide composition of the present invention contains no surfactant other than the selected surfactant or surfactant mixture (i), (ii), (iii), (iv), or (vi).

In one embodiment, the pesticide composition of the present invention contains no surfactant.

In one embodiment, the pesticide composition of the present invention comprises, based on 100 pbw of the pesticide composition:

(a) from about 15 pbw, more typically from about 30 pbw, and even more typically from about 40 pbw, to about 65 pbw, more typically to about 60 pbw, and even more typically to about 55 pbw, of the one or more pesticide compounds,
(b) from greater than 0 pbw, more typically from about 0.001 pbw and even more typically from about 0.005 pbw, to about 10 pbw, more typically to about 8 pbw, and even more typically to about 6 pbw, of the one or more fatty acid $(C_1-C_3)$ alkyl esters,
(c) from greater than 0 pbw, more typically from about 0.5 pbw and even more typically from about 1 pbw, to about 20 pbw, more typically to about 10 pbw, and even more typically to about 8 pbw of the one or more surfactants selected from:
(i) one or more betaine surfactants,
(ii) one or more glycoside surfactants,
(iii) one or more amine oxide surfactants,
(iv) one or more fatty (ether) amine alkoxylate surfactants, and
(v) a surfactant mixture comprising at least one surfactant from each of at least two of the surfactant categories (i), (ii), (iii), and (iv), and
(d) from greater than 0 pbw, more typically from about 5 pbw, to about 70 pbw, more typically to less than 70 pbw water.

In one embodiment, the pesticide composition of the present invention comprises from about 0.002 pbw, more typically from about 0.2 pbw to about 2.0, more typically to about 1.0 pbw, of the one or more fatty acid $(C_1-C_3)$ alkyl esters per 100 pbw of the one or more pesticide compounds.

In one embodiment, the pesticide composition of the present invention comprises from about 2 more typically from about 4 to about 5 pbw, more typically to about 10 pbw, of the one or more surfactants per 100 pbw of the one or more pesticide compounds.

The pesticide composition of the present invention typically comprises from greater than 0 to less than 70 pbw, more typically from about 5 to about 70 pbw water and may, optionally, further comprise one or more agronomically acceptable solvent or carrier in addition to water. Suitable solvents include water miscible organic solvents, such as alcohols, more typically $(C_1-C_8)$alcohols, such as ethanol, glycols, such as ethylene glycol, and polyglycols, such as polyethylene glycol, and N-alkyl pyrrolidones, as well as water immiscible organic solvents, such as, for example, alkylated aromatic solvents, such as toluene or alkylated naphthalenes and mineral oil fractions, such as paraffinic hydrocarbons.

In one embodiment, the pesticide composition of the present invention comprises a surfactant mixture comprising:
(v.1) one or more betaine surfactants and one or more glycoside surfactants, more typically, based on 100 pbw of the surfactant mixture, from about 70 pbw, more typically from about 80 pbw, even more typically from about 90 pbw, to less than 100 pbw, more typically to about 98 pbw, even more typically to about 97 pbw, of one or more betaine surfactants and from greater than 0, more typically from about 2 pbw, even more typically from about 3 pbw, to about 30 pbw, more typically to about 20 pbw, even more typically to about 10 pbw, of one or more glycoside surfactants, or
(v.2) one or more betaine surfactants and one or more amine oxide surfactants, more typically, based on 100 pbw of the surfactant mixture, from about 50 pbw, more typically from about 75 pbw, even more typically from about 90 pbw, to less than 100 pbw, more typically to about 98 pbw, even more typically to about 97 pbw, of one or more betaine surfactants and from greater than 0 pbw, more typically from about 2 pbw, even more typically from about 3 pbw, to about 50 pbw, more typically to about 25 pbw, even more typically to about 10 pbw, of one or more amine oxide surfactants, or (v.3) one or more betaine surfactants and one or more fatty (ether) amine alkoxylate surfactants more typically, based on 100 pbw of the surfactant mixture, from about 50 pbw, more typically from about 55 pbw, even more typically from about 60 pbw, to about 90 pbw, more typically to about 80 pbw, even more typically to about 75 pbw, of one or more betaine surfactants from about 10 pbw, more typically from about 20 pbw, even more typically from about 25 pbw, to about 50 pbw, more typically to about 45 pbw, even more typically to about 40 pbw, of one or more fatty (ether) amine alkoxylate surfactants, or (v.4) one or more glycoside surfactants and one or more amine oxide surfactants, more typically, based on 100 pbw of the surfactant mixture, from greater than 0 pbw, more typically from about 2 pbw, even more typically from about 3 pbw, to about 30 pbw, more typically to about 25 pbw, even more typically to about 10 pbw, of one or more glycoside surfactants and from about 70 pbw, more typically from about 75 pbw, even more typically from about 90 pbw, to less than 100 pbw, more typically to about 98 pbw, even more typically to about 97 pbw, of one or more amine oxide surfactants, or (v.5) one or more glycoside surfactants and one or more fatty (ether) amine alkoxylate surfactants, more typically, based on 100 pbw of the surfactant mixture, from greater than 0 pbw, more typically from about 2 pbw, even more typically from about 3 pbw, to 30 pbw, more typically to about 25 pbw, even more typically to about 10 pbw, of one or more glycoside surfactants and from about 70 pbw, more typically from about 75 pbw, even more typically from about 90 pbw, to less than 100 pbw, more typically to about 98 pbw, even more typically to about 97 pbw, of one or more fatty (ether) amine alkoxylate surfactants, or (v.6) one or more amine oxide surfactants and one or more fatty (ether) amine alkoxylate surfactants, more typically, based on 100 pbw of the surfactant mixture, from about 35 pbw, more typically from about 40 pbw, even more typically from about 45 pbw, to about 65 pbw, more typically to about 60 pbw, even more typically to about 55 pbw of one or more amine oxide surfactants and from about 35 pbw, more typically from about 40 pbw, even more typically from about 45 pbw, to about 65 pbw, more typically to about 60 pbw, even more typically to about 55 pbw of one or more fatty (ether) amine alkoxylate surfactants.

In one embodiment, the pesticide composition of the present invention comprises, based on 100 pbw of the composition:

(a) from about 15 pbw, more typically from about 30 pbw, and even more typically from about 40 pbw, to about 65 pbw, more typically to about 60 pbw, and even more typically to about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof, (b) from greater than 0 pbw, more typically from about 0.001 pbw and even more typically from about 0.005 pbw, to about 10 pbw, more typically to about 8 pbw, and even more typically to about 6 pbw, of one or more fatty acid $(C_1$-$C_3)$ esters, more typically, one or more methylated vegetable oils (c) from greater than 0 pbw, more typically from about 0.5 pbw and even more typically from about 1 pbw, to about 20 pbw, more typically to about 10 pbw, and even more typically to about 8 pbw of one or more betaine surfactants, and still more typically, one or more $(C_{12}$-$C_{14})$alkyl dimethyl betaine surfactants, (d) optionally from greater than 0 pbw, more typically from about 0.5 pbw, and even more typically from about 1 pbw, to about 20 pbw, more typically to about 10 pbw, and even more typically to about 8 pbw, of a polyhydric alcohol, more typically, glycerine, and (e) from greater than 0 pbw, more typically from about 5 pbw, to about 70 pbw, more typically to less than 70 pbw, water.

In one embodiment, the pesticide composition of the present invention comprises, based on 100 pbw of the composition:

(a) from about 15 pbw, more typically from about 30 pbw, and even more typically from about 40 pbw, to about 65 pbw, more typically to about 60 pbw, and even more typically to about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof, (b) from greater than 0 pbw, more typically from about 0.001 pbw and even more typically from about 0.005 pbw, to about 10 pbw, more typically to about 8 pbw, and even more typically to about 6 pbw, of one or more fatty acid $(C_1$-$C_3)$ esters, more typically, one or more methylated vegetable oils (c) from greater than 0 pbw, more typically from about 0.5 pbw and even more typically from about 1 pbw, to about 20 pbw, more typically to about 10 pbw, and even more typically to about 8 pbw, of one or more glycoside surfactants, more typically, one or more alkyl polyglucoside surfactants, and (d) from greater than 0 pbw, more typically from about 5 pbw, to about 70 pbw, more typically to less than 70 pbw, water.

In one embodiment, the pesticide composition of the present invention comprises, based on 100 pbw of the composition:

(a) from about 15 pbw, more typically from about 30 pbw, and even more typically from about 40 pbw, to about 65 pbw, more typically to about 60 pbw, and even more typically to about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof, (b) from greater than 0 pbw, more typically from about 0.001 pbw and even more typically from about 0.005 pbw, to about 10 pbw, more typically to about 8 pbw, and even more typically to about 6 pbw, of one or more fatty acid $(C_1$-$C_3)$ esters, more typically, one or more methylated vegetable oils, (c) from greater than 0 pbw, more typically from about 0.5 pbw and even more typically from about 1 pbw, to about 20 pbw, more typically to about 10 pbw, and even more typically to about 8 pbw, of one or more amine oxide surfactants, more typically, one or more $(C_8$-$C_{18})$alkyl dimethyl amine oxide surfactants, and (d) from greater than 0 pbw, more typically from about 5 pbw, to about 70 pbw, more typically to less than 70 pbw, water.

In one embodiment, the pesticide composition of the present invention comprises, based on 100 pbw of the composition:

(a) from about 15 pbw, more typically from about 30 pbw, and even more typically from about 40 pbw, to about 65 pbw, more typically about 60 pbw, and even more typically about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof, (b) from greater than 0 pbw, more typically from about 0.001 pbw and even more typically from about 0.005 pbw, to about 10 pbw, more typically about 8 pbw, and even more typically about 6 pbw, of one or more fatty acid ($C_1$-$C_3$) esters, more typically, one or more methylated vegetable oils, (c) from greater than 0 pbw, more typically from about 0.5 pbw and even more typically from about 1 pbw, to about 20 pbw, more typically about 10 pbw, and even more typically about 8 pbw, of one or mote fatty (ether) amine alkoxylate surfactants, more typically, one or more ($C_8$-$C_{22}$)alkyl amine alkoxylate surfactants, and (d) from greater than 0 pbw, more typically from about 5 pbw, to about 70 pbw, more typically to less than 70 pbw, water.

In one embodiment, the pesticide composition of the present invention comprises, based on 100 pbw of the composition:

(a) from about 15 pbw, more typically from about 30 pbw, and even more typically from about 40 pbw, to about 65 pbw, more typically about 60 pbw, and even more typically about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof, (b) from greater than 0 pbw, more typically from about 0.001 pbw and even more typically from about 0.005 pbw, to about 10 pbw, more typically about 8 pbw, and even more typically about 6 pbw, of one or more fatty acid ($C_1$-$C_3$) esters, more typically, one or more methylated vegetable oils, (c) from greater than 0 pbw, more typically from about 0.5 pbw and even more typically from about 1 pbw, to about 20 pbw, more typically about 10 pbw, and even more typically about 8 pbw, of a surfactant mixture comprising from about 70 pbw, more typically from about 80 pbw, even more typically from about 90 pbw, to less than 100 pbw, more typically to about 98 pbw, even more typically to about 97 pbw, of one or more betaine surfactants, more typically, one or more ($C_{12}$-$C_{14}$)alkyl dimethyl betaine surfactants, and from greater than 0, more typically from about 2 pbw, even more typically from about 3 pbw, to about 30 pbw, more typically to about 20 pbw, even more typically to about 10 pbw, of one or more glycoside surfactants, more typically, one or more alkyl polyglucoside surfactants, (d) optionally from greater than 0 pbw, more typically from about 0.5 pbw, and even more typically from about 1 pbw, to about 20 pbw, more typically about 10 pbw, and even more typically about 8 pbw, of a polyhydric alcohol, more typically, glycerine, and (e) from greater than 0 pbw, more typically from about 5 pbw, to about 70 pbw, more typically to less than 70 pbw, water.

In one embodiment, the pesticide composition of the present invention comprises, based on 100 pbw of the composition:

(a) from about 15 pbw, more typically from about 30 pbw, and even more typically from about 40 pbw, to about 65 pbw, more typically about 60 pbw, and even more typically about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof, (b) from greater than 0 pbw, more typically from about 0.001 pbw and even more typically from about 0.005 pbw, to about 10 pbw, more typically about 8 pbw, and even more typically about 6 pbw, of one or more fatty acid ($C_1$-$C_3$) esters, more typically, one or more methylated vegetable oils, (c) from greater than 0 pbw, more typically from about 0.5 pbw and even more typically from about 1 pbw, to about 20 pbw, more typically about 10 pbw, and even more typically about 8 pbw, of a surfactant mixture comprising from about 50 pbw, more typically from about 75 pbw, even more typically from about 90 pbw, to less than 100 pbw, more typically to about 98 pbw, even more typically to about 97 pbw, of one or more betaine surfactants, more typically, one or more ($C_{12}$-$C_{14}$)alkyl dimethyl betaine surfactants, and from greater than 0 pbw, more typically from about 2 pbw, even more typically from about 3 pbw, to about 50 pbw, more typically to about 25 pbw, even more typically to about 10 pbw, of one or more amine oxide surfactants, more typically, one or more ($C_8$-$C_{18}$)alkyl dimethyl amine oxide surfactants, (d) optionally from greater than 0 pbw, more typically from about 0.5 pbw, and even more typically from about 1 pbw, to about 20 pbw, more typically about 10 pbw, and even more typically about 8 pbw, of a polyhydric alcohol, more typically, glycerine, and (e) from greater than 0 pbw, more typically from about 5 pbw, to about 70 pbw, more typically to less than 70 pbw, water.

In one embodiment, the pesticide composition of the present invention comprises, based on 100 pbw of the composition:

(a) from about 15 pbw, more typically from about 30 pbw, and even more typically from about 40 pbw, to about 65 pbw, more typically about 60 pbw, and even more typically about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof, (b) from greater than 0 pbw, more typically from about 0.001 pbw and even more typically from about 0.005 pbw, to about 10 pbw, more typically about 8 pbw, and even more typically about 6 pbw, of one or more fatty acid ($C_1$-$C_3$) esters, more typically one or more methylated vegetable oils, (c) from greater than 0 pbw, more typically from about 0.5 pbw and even more typically from about 1 pbw, to about 20 pbw, more typically about 10 pbw, and even more typically about 8 pbw, of a surfactant mixture comprising from about 50 pbw, more typically from about 55 pbw, even more typically from about 60 pbw, to about 90 pbw, more typically to about 80 pbw, even more typically to about 75 pbw, of one or more betaine surfactants, more typically, one or more ($C_{12}$-$C_{14}$)alkyl dimethyl betaine surfactants and from about 10 pbw, more typically from about 20 pbw, even more typically from about 25 pbw, to about 50 pbw, more typically to about 45 pbw, even more typically to about 40 pbw, of one or more fatty (ether) amine alkoxylate surfactants, more typically, one or more ($C_8$-$C_{22}$)alkyl amine alkoxylate surfactants, (d) optionally from greater than 0 pbw, more typically from about 0.5 pbw, and even more typically from about 1 pbw, to about 20 pbw, more typically about 10 pbw, and even more typically about 8 pbw, of a polyhydric alcohol, more typically, glycerine, and (e) from greater than 0 pbw, more typically from about 5 pbw, to about 70 pbw, more typically to less than 70 pbw, water.

In one embodiment, the pesticide composition of the present invention comprises, based on 100 pbw of the composition:
(a) from about 15 pbw, more typically from about 30 pbw, and even more typically from about 40 pbw, to about 65 pbw, more typically about 60 pbw, and even more typically about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof,
(b) from greater than 0 pbw, more typically from about 0.001 pbw and even more typically from about 0.005 pbw, to about 10 pbw, more typically about 8 pbw, and even more typically about 6 pbw, of one or more fatty acid ($C_1$-$C_3$) esters, more typically, one or more methylated vegetable oils,
(c) from greater than 0 pbw, more typically from about 0.5 pbw and even more typically from about 1 pbw, to about 20 pbw, more typically about 10 pbw, and even more typically about 8 pbw, of a surfactant mixture comprising from greater than 0 pbw, more typically from about 2 pbw, even more typically from about 3 pbw, to about 30 pbw, more typically to about 25 pbw, even more typically to about 10 pbw, of one or more glycoside surfactants, more typically, one or more alkyl polyglucoside surfactants, and from about 70 pbw, more typically from about 75 pbw, even more typically from about 90 pbw, to less than 100 pbw, more typically to about 98 pbw, even more typically to about 97 pbw, of one or more amine oxide surfactants, more typically, one or more ($C_8$-$C_{18}$)alkyl dimethyl amine oxide surfactants, and
(d) from greater than 0 pbw, more typically from about 5 pbw, to about 70 pbw, more typically to less than 70 pbw, water.

In one embodiment, the pesticide composition of the present invention comprises, based on 100 pbw of the composition:
(a) from about 15 pbw, more typically from about 30 pbw, and even more typically from about 40 pbw, to about 65 pbw, more typically about 60 pbw, and even more typically about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof,
(b) from greater than 0 pbw, more typically from about 0.001 pbw and even more typically from about 0.005 pbw, to about 10 pbw, more typically about 8 pbw, and even more typically about 6 pbw, of one or more fatty acid ($C_1$-$C_3$) esters, more typically, one or more methylated vegetable oils
(c) from greater than 0 pbw, more typically from about 0.5 pbw and even more typically from about 1 pbw, to about 20 pbw, more typically about 10 pbw, and even more typically about 8 pbw, of a surfactant mixture comprising from greater than 0 pbw, more typically from about 2 pbw, even more typically from about 3 pbw, to 30 pbw, more typically to about 25 pbw, even more typically to about 10 pbw, of one or more glycoside surfactants, more typically, one or more alkyl polyglucoside surfactants, and from about 70 pbw, more typically from about 75 pbw, even more typically from about 90 pbw, to less than 100 pbw, more typically to about 98 pbw, even more typically to about 97 pbw, of one or more fatty (ether) amine alkoxylate surfactants, more typically, one or more ($C_8$-$C_{22}$)alkyl amine alkoxylate surfactants, and
(d) from greater than 0 pbw, more typically from about 5 pbw, to about 70 pbw, more typically to less than 70 pbw, water.

In one embodiment, the pesticide composition of the present invention comprises, based on 100 pbw of the composition:
(a) from about 15 pbw, more typically from about 30 pbw, and even more typically from about 40 pbw, to about 65 pbw, more typically about 60 pbw, and even more typically about 55 pbw, of one or more pesticide compounds, more typically of one or more herbicide compounds, even more typically one or more herbicide compounds selected from glyphosate, glufosinate, dicamba, 2,4-D, their respective water soluble salts and esters, and mixtures thereof,
(b) from greater than 0 pbw, more typically from about 0.001 pbw and even more typically from about 0.005 pbw, to about 10 pbw, more typically about 8 pbw, and even more typically about 6 pbw, of one or more fatty acid ($C_1$-$C_3$) esters, more typically, one or more methylated vegetable oils,
(c) from greater than 0 pbw, more typically from about 0.5 pbw and even more typically from about 1 pbw, to about 20 pbw, more typically about 10 pbw, and even more typically about 8 pbw, of a surfactant mixture comprising from about 35 pbw, more typically from about 40 pbw, even more typically from about 45 pbw, to about 65 pbw, more typically to about 60 pbw, even more typically to about 55 pbw of one or more amine oxide surfactants, more typically, one or more ($C_8$-$C_{18}$)alkyl dimethyl amine oxide surfactants, and from about 35 pbw, more typically from about 40 pbw, even more typically from about 45 pbw, to about 65 pbw, more typically to about 60 pbw, even more typically to about 55 pbw of one or more fatty (ether) amine alkoxylate surfactants, more typically, one or more ($C_8$-$C_{22}$)alkyl amine alkoxylate surfactants, and
(d) from greater than 0 pbw, more typically from about 5 pbw, to about 70 pbw, more typically to less than 70 pbw, water.

In one embodiment, the pesticide composition of the present invention exhibits a viscosity at 25° C. of less than or equal to about 400 centiPoise ("cP"), more typically from about 25 to about 300 cP, and even more typically from about 50 to about 250 cP.

In one embodiment, the pesticide composition of the present invention exhibits a viscosity at 5° C. of less than or equal to about 1200 cP, more typically from about 100 to about 800 cP, and even more typically from about 200 to about 500 cP In one embodiment, the pesticide composition of the present invention is substantially homogeneous in visual appearance. In one embodiment, the pesticide composition of the present invention is in the form of a single liquid phase that is homogeneous, clear, and transparent in visual appearance.

The pesticide composition of the present invention exhibits good storage stability. The criteria for assessing storage stability are that the composition remains substantially homogeneous in visual appearance during storage and does not separate into layers of mutually insoluble liquid phases and does not form any solid precipitate upon quiescent standing. In one embodiment, the pesticide composition remains stable during storage at temperatures from 0° C. to 54° C. for greater than or equal to 7 days, more typically for greater than or equal to 8 days and even more typically for greater than or equal to 30 days. The pesticide composition typically remains stable during continuous freeze-thaw cycling for greater than or equal to 7 days, more typically for greater than or equal to 8 days and even more typically for greater than or equal to 30 days, wherein one freeze-thaw cycle consists of a four hour dwell at a temperature of from −12° C. to −10° C., an eight hour ramp to 25° C., a four hour dwell at 25° C. and an eight hour ramp back to −12° C. to −10° C.

The pesticide composition of the present invention is made by combining and mixing the respective ingredients together. In one embodiment, the pesticide composition is made by combining and mixing an adjuvant composition that comprises the fatty acid ($C_1$-$C_3$) ester component and any optional surfactant component of the pesticide composition of the present invention, a pesticide compound, and, typically, water. Alternatively, the pesticide composition is made by combining and mixing the separate components of the adjuvant composition, the pesticide, and water.

In one embodiment, the present invention is directed to a an adjuvant composition comprising:
(a) from greater than 0 pbw, more typically from about 0.1 pbw and even more typically from about 0.5 pbw, to about 10 pbw, more typically about 8 pbw, and even more typically about 6 pbw, of one or more fatty acid ($C_1$-$C_3$) esters,
(b) from about 10 pbw, more typically from about 15 pbw and even more typically from about 18 pbw, to about 90 pbw, more typically about 80 pbw, and even more typically about 75 pbw, of the one or more surfactants selected from:
  (i) one or more betaine surfactants,
  (ii) one or more glycoside surfactants,
  (iii) one or more amine oxide surfactants,
  (iv) one or more fatty (ether) amine alkoxylate surfactants, and
  (v) a surfactant mixture comprising at least one surfactant from each of at least two of the surfactant categories (i), (ii), (iii), and (iv), and
(c) from greater than 0 pbw, more typically from about 5 pbw, and even more typically from about 10 pbw, to about 70 pbw, more typically to about 75 pbw, and even more typically to about 60 pbw, water.

In one embodiment, the present invention is directed to a method for making a pesticide composition, comprising:
(1) providing an adjuvant composition comprising:
  (a) from greater than 0 pbw, more typically from about 0.1 pbw and even more typically from about 0.5 pbw, to about 10 pbw, more typically about 8 pbw, and even more typically about 6 pbw, of one or more fatty acid ($C_1$-$C_3$) esters,
  (b) from about 10 pbw, more typically from about 15 pbw and even more typically from about 18 pbw, to about 90 pbw, more typically about 80 pbw, and even more typically about 75 pbw, of the one or more surfactants selected from:
    (i) one or more betaine surfactants,
    (ii) one or more glycoside surfactants,
    (iii) one or more amine oxide surfactants,
    (iv) one or more fatty (ether) amine alkoxylate surfactants, and
    (v) a surfactant mixture comprising at least one surfactant from each of at least two of the surfactant categories (i), (ii), (iii), and (iv), and
  (b) from greater than 0 pbw, more typically from about 5 pbw, and even more typically from about 10 pbw, to about 70 pbw, more typically to about 75 pbw, and even more typically to about 60 pbw, water, and
(2) mixing the adjuvant composition with one or more pesticide compounds and, optionally, water, to provide a pesticide composition that comprises, based on 100 pbw of the pesticide composition:
  (a) from about 15 pbw, more typically from about 30 pbw, and even more typically from about 40 pbw, to about 65 pbw, more typically to about 60 pbw, and even more typically to about 55 pbw, of the one or more pesticide compounds,
  (b) from greater than 0 pbw, more typically from about 0.001 pbw and even more typically from about 0.005 pbw, to about 10 pbw, more typically to about 8 pbw, and even more typically to about 6 pbw, of the one or more fatty acid ($C_1$-$C_3$) esters, and
  (c) from greater than 0 pbw, more typically from about 0.5 pbw and even more typically from about 1 pbw, to about 20 pbw, more typically to about 10 pbw, and even more typically to about 8 pbw of the one or more surfactants.

In one embodiment, wherein the surfactant component of the pesticide composition comprises one or more glycoside surfactants, the pesticide composition comprises, based on 100 pbw of the pesticide composition, less than 4 pbw, more typically less than 1 pbw, and even more typically, 0 pbw, of any lipophilic emulsifier, such as, for example, fatty acid polyol partial esters, fatty alcohols and fatty alcohol polyethers, or a mixture thereof.

In one embodiment, the concentrated pesticide composition of the present invention is a concentrated herbicide composition that exhibits good stability and handling properties, including low viscosity, and is intended to be diluted with an aqueous diluent prior to application to a target plant and/or the environment of the target plant. Suitable aqueous diluents comprise water and may optionally further comprise one or more water miscible organic liquids, such as, for example, alcohols, for example, methanol, ethanol, or propanol, glycols, for example, ethylene glycol, propylene glycol, or butylene glycol, and/or alkylether diols for example, ethylene glycol monoethyl ether, propylene glycol monoethyl ether and diethylene glycol monomethyl ether. Most typically, the aqueous diluent is water.

In one embodiment, the present invention is directed to a method for making a pesticide composition at the point of use, comprising:
(1) providing a pesticide concentrate composition comprising, based on 100 pbw of the composition:
  (a) from about 15 pbw, more typically from about 30 pbw, and even more typically from about 40 pbw, to about 65 pbw, more typically to about 60 pbw, and even more typically to about 55 pbw, of one or more pesticide compounds,
  (b) from greater than 0 pbw, more typically from about 0.001 pbw and even more typically from about 0.005 pbw, to about 10 pbw, more typically to about 8 pbw, and even more typically to about 6 pbw, of one or more fatty acid ($C_1$-$C_3$) esters, and
  (c) optionally, from greater than 0 pbw, more typically from about 0.5 pbw and even more typically from about 1 pbw, to about 20 pbw, more typically to about 10 pbw, and even more typically to about 8 pbw of one or more surfactants, and
  said pesticide composition having a viscosity of less than or equal to 1200 cP at 5° C., and
(2) diluting the pesticide concentrate composition with an aqueous diluent, typically with water, to provide a diluted pesticide composition, comprising:
  (a) from greater than 0 to about 5 pbw of the one or more pesticide compounds,
  (b) from greater than 0 to about 0.8 pbw of the one or more fatty acid ($C_1$-$C_3$) esters, and
  (c) optionally, up to about 1.6 pbw of the one or more surfactants.

In one embodiment, the pesticide composition of the present invention is a pesticide concentrate composition and is diluted with water, typically in a ratio of from 1:10 to 1:100 pbw pesticide concentrate composition: pbw water to form a pesticide "spray mix" composition for applying to target pests.

In one embodiment, the present invention is directed to a method for controlling a target pest, comprising:

(1) providing a pesticide concentrate composition comprising, based on 100 pbw of the composition:
  - (a) from about 15 pbw, more typically from about 30 pbw, and even more typically from about 40 pbw, to about 65 pbw, more typically to about 60 pbw, and even more typically to about 55 pbw, of one or more pesticide compounds,
  - (b) from greater than 0 pbw, more typically from about 0.001 pbw and even more typically from about 0.005 pbw, to about 10 pbw, more typically to about 8 pbw, and even more typically to about 6 pbw, of one or more fatty acid ($C_1$-$C_3$) esters, and
  - (c) optionally, from greater than 0 pbw, more typically from about 0.5 pbw and even more typically from about 1 pbw, to about 20 pbw, more typically to about 10 pbw, and even more typically to about 8 pbw of one or more surfactants, and said pesticide composition having a viscosity of less than or equal to 1200 cP at 5° C., (2) diluting the pesticide concentrate composition with an aqueous diluent, typically with water, to provide a diluted pesticide composition, comprising:
  - (a) from greater than 0 to about 5 pbw of the one or more pesticide compounds,
  - (b) from greater than 0 to about 0.8 pbw of the one or more fatty acid ($C_1$-$C_3$) esters, and
  - (c) optionally, up to about 1.6 pbw of the one or more surfactants, and (3) applying the diluted pesticide composition to the target pest and/or to the environment of the target pest.

In one embodiment, the pesticide composition further comprises a fertilizer. Such fertilizers can provide the primary nutrients of nitrogen, phosphorus and/or potassium such as urea ammonium nitrate (30-0-0), 10-34-0, secondary nutrients sulfur, calcium, magnesium such as ammonium thiosulfate 12-0-0-26S, micronutrient fertilizers containing zinc, iron, molybdenum, copper, boron, chlorine, magnesium, for example, 0-0-1 3%-S; 3%-Zn; 2%-Fe; 2%-Mn and mixtures thereof. In one embodiment, the pesticide composition comprises from about 85 to about 99 pbw, more typically from about 90 to about 99 pbw, and even more typically from about 93 to about 99 pbw, of a mixture of fertilizer and water.

In one embodiment, the pesticide composition of the present invention further comprises one or more water conditioners, such as for example, chelating agents, such as ethylenediamine tetraacetic acid, complexing agents such as ammonium sulfate, and pH adjusting agents, such as citric acid and polyacrylic acid or other ingredients, such as for example, one or more thickeners, such as polysaccharide thickeners, and polyacrylamide thickeners, as well as antifoams, spreaders, and drift control agents.

In one embodiment, the pesticide composition of the present invention comprises, based on 100 pbw of such composition, from about 0.1 to about 3 pbw, more typically from about 0.7 to about 2.5 pbw, of one or more water conditioners, typically ammonium sulfate.

In one embodiment, the concentrated pesticide composition of the present invention is a concentrated herbicide composition that, when diluted and applied to the target plant and/or the environment of the target plant in a herbicidally effective amount is effective to control one or more target plant species of one or more of the following genera: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*, including annual broadleaf species such as, for example, velvetleaf (*Abutilon theophrasti*), pigweed (*Amaranthus* spp.), buttonweed (*Borreria* spp.), oilseed rape, canola, Indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), *sida* (*Sida* spp.), wild mustard (*Sinapis arvensis*) and cocklebur (*Xanthium* spp.), annual narrowleaf species such as for example, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*), perennial broadleaf species such as, for example, mugwort (*Artemisia* spp.), milkweed (*Asclepias* spp.), canada thistle (*Cirsium arvense*), field bindweed (*Convolvulus arvensis*) and kudzu (*Pueraria* spp.), perennial narrowleaf species such as for example, *brachiaria* (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.), and other perennial species such as, for example, horsetail (*Equisetum* spp.), bracken (*Pteridium aquilinum*), blackberry (*Rubus* spp.) and gorse (*Ulex europaeus*).

In one embodiment, the pesticide composition of the present invention is applied to foliage of a target plant at a rate of from about 0.25 pint, more typically about 0.5 pint, to about 5 pints, even more typically from about 1 pint to about 4 pints, as expressed in terms of the above described pesticide concentrate composition embodiment of the pesticide composition of the present invention (that is, comprising, based on 100 pbw of such composition, from about 30 to about 65 pbw) per acre.

In one embodiment, the pesticide composition is spray applied via conventional spray apparatus to foliage of one or more target plants present on an area of ground at a rate of from about 1 gallon to about 20 gallons, more typically about 3 gallons to 20 gallons, of the above described spray mix embodiment of the pesticide composition per acre of ground.

The concentrated pesticide composition of the present invention exhibits good stability and handling properties, including low viscosity, and can be readily diluted with water to form efficacious aqueous pesticide compositions that may be spray applied to target pests and/or the environment of the target pests.

Examples 1-5 and Comparative Examples C1-C6

The pesticide compositions of Examples 1-5 and Comparative Examples C1-C6, each containing about 540 grams per Liter ("g/L") glyphosate dimethyl amine salt (corresponding to 360 g/L glyphosate as acid equivalent) and 100 g/L of a surfactant component comprising a betaine surfactant component (either an aqueous composition comprising about 14 wt % ($C_{12}$-$C_{14}$)alkyldimethyl betaines and about 50 wt % glycerol ("BET-A") or an aqueous composition comprising about 30 wt % ($C_{12}$-$C_{14}$)alkyldimethyl betaines ("BET-B")), a mixture of alkyl polyglucoside (70% aqueous, Cognis Agnique P8107 ("APG")) and BET-A or BET-B, or a mixture of fatty acid methyl ester (Amesolv CME ("FAME-1")), BET-A or BET-B, and APG, were made by mixing 110.25 grams of a 62%, aqueous solution of glyphosate, dimethyl amine salt with 10.00 grams of a surfactant blend and then diluting the glyphosate/surfactant mixture to 100 milliliters with water. The viscosity the pesticide compositions was measured using a Brookfield rotational viscometer at room temperature and at 5° C. The composition of the surfactant mixture used in each of the pesticide compositions of Examples 1-5 and Comparative Examples $C_1$-$C_6$, as grams of each component per 10 grams of surfactant mixture, and the viscosity of each the compositions at room temperature ("RT") and at 5° C. are set forth below in TABLES I and II.

TABLE I

Composition of the Surfactant Component of Aqueous Pesticide Compositions containing 540 g/L Glyphosate Dimethyl Amine Salt and 100 g/L of the Surfactant Component, and Viscosity of such Aqueous Pesticide Compositions

| | Example # | | | | | | |
|---|---|---|---|---|---|---|---|
| | 1 | 2 | 3 | 4 | C1 | C2 | C3 |
| BET-A (g) | 9.0 | 9.8 | 9.5 | 9.8 | 9.0 | 9.5 | 10.0 |
| APG (g) | 0.5 | 0.1 | 0.4 | 0.15 | 1.0 | 0.5 | 0 |
| FAME-1 (g) | 0.5 | 0.1 | 0.1 | 0.05 | 0 | 0 | 0 |
| Viscosity, RT (cP) | 76 | 80.6 | 96.9 | 81.6 | 132 | 160 | 93.6 |
| Viscosity, 5° C. (cP) | 189.9 | 213.9 | 306.5 | 289.7 | 226.2 | 438.5 | 283.7 |

TABLE II

Composition of the Surfactant Component of Aqueous Pesticide Compositions containing 540 g/L Glyphosate Dimethyl Amine Salt and 100 g/L of the Surfactant Component, and Viscosity of such Aqueous Pesticide Compositions

| | Example # | | | |
|---|---|---|---|---|
| | 5 | C4 | C5 | C6 |
| BET-B (g) | 9.0 | 9.0 | 9.5 | 10.0 |
| APG (g) | 0.5 | 1.0 | 0.5 | 0 |
| FAME-1 (g) | 0.5 | 0 | 0 | 0 |
| Viscosity, RT (cP) | 91 | 379 | 457 | 206 |
| Viscosity, 5° C. (cP) | 256 | — | — | 1104 |

Example 7 and Comparative Example C7

The pesticide compositions of Example 7 and Comparative Example C7, each containing about 540 g/L glyphosate, as glyphosate acid, 210 g/L KOH and 160 g/L of a surfactant component comprising an aqueous composition comprising about 30 wt % amine oxide surfactant ($C_{12}$-$C_{14}$)alkyl dimethyl amine oxide ("AO")) or a mixture of fatty acid methyl ester (Amesolv CME ("FAME-1")), and AO were made by mixing 567 grams of a 95.3% aqueous solution of glyphosate acid, 420 grams of a 50% aqueous solution of KOH, and 160 grams surfactant component and then diluting the glyphosate/KOH/surfactant mixture to 1 Liter with water. The viscosity the pesticide compositions was measured using a Brookfield rotational viscometer at 4° C. The composition of the surfactant mixture used in each of the pesticide compositions of Example 7 and Comparative Example C7, as grams of each component per 100 grams of surfactant mixture, and the viscosity of each the compositions at 4° C. are set forth below in TABLE III and II. The composition of Example 7 was visually clear and transparent at −5° C., 0° C., and 54° C.

TABLE III

Composition of Surfactant Component of Aqueous Pesticide Compositions containing 540 g/L Glyphosate Dimethyl Amine Salt, 210 g/L KOH, and 100 g/L of the Surfactant Component, and the Viscosity of such Aqueous Pesticide Compositions

| | 7 | C7 |
|---|---|---|
| AO, 30% aqueous solution (g) | 91 | 100 |
| FAME-1 (g) | 9 | 0 |
| Viscosity, 4° C. (cP) | 60 | gel |

The invention claimed is:

1. A pesticide composition, comprising, based on 100 parts by weight ("pbw") of the composition:
   (a) from about 15 to about 65 pbw of one or more herbicide compounds selected from glyphosate, glufosinate, their respective water soluble salts and esters, and mixtures thereof,
   (b) from greater than 0 to about 10 pbw of one or more fatty acid ($C_1$-$C_3$)alkyl esters according to structure (I):

wherein:
   $R^{11}$ is ($C_6$-$C_{24}$)alkyl or ($C_6$-$C_{24}$)alkenyl, and
   $R^{12}$ is ($C_1$-$C_3$)alkyl, and
   (c) from greater than 0 to about 20 pbw of one or more surfactants selected from:
      (i) one or more ($C_{12}$-$C_{14}$)alkyldimethyl betaine surfactants,
      (ii) one or more alkylpolyglucoside surfactants,
      (iii) one or more ($C_{12}$-$C_{14}$)alkyldimethyl amine oxide surfactants, and
      (iv) a surfactant mixture comprising at least one surfactant from each of at least two of the surfactant categories (i), (ii), and (iii).

2. The composition of claim 1, wherein the pesticide composition is an aqueous composition.

3. The composition of claim 1, wherein $R^{12}$ is methyl.

4. The composition of claim 1, wherein the fatty acid ($C_1$-$C_3$)alkyl ester comprises one or more ($C_1$-$C_3$)alkyl vegetable oils.

5. The composition of claim 1, wherein composition comprises the one or more betaine surfactants.

6. The composition of claim 5, wherein the composition further comprises a polyhydric alcohol.

7. The composition of claim 1, wherein composition comprises one or more alkylpolyglucoside surfactants.

8. The composition of claim 1, wherein composition comprises the one or more amine oxide surfactants.

9. The composition of claim 1, wherein the composition comprises a mixture of the one or more betaine surfactants and the one or more alkylpolyglucoside surfactants.

10. The composition of claim 9, wherein the composition further comprises a polyhydric alcohol.

11. A method for controlling a target plant, comprising diluting the pesticide composition of claim 1 with a diluent comprising water and applying the diluted pesticide composition to the target plant and/or the environment of the target plant.

12. An pesticide composition comprising, based on 100 pbw of the pesticide composition:
   (a) from about 15 pbw to about 65 pbw of one or more herbicide compounds selected from glyphosate, glufosinate, their respective water soluble salts and esters, and mixtures thereof,
   (b) from greater than 0 pbw to about 10 pbw of one or more fatty acid methyl esters,
   (c) from greater than 0 pbw to about 20 pbw of one or more surfactants selected from:
      (i) one or more $(C_{12}-C_{14})$alkyldimethyl betaine surfactants,
      (ii) one or more alkylpolyglucoside surfactants,
      (iii) one or more $(C_{12}-C_{14})$alkyldimethyl amine oxide surfactants, and
      (iv) a surfactant mixture comprising at least one surfactant from each of at least two of the surfactant categories (i), (ii), and (iii), and
   (d) from greater than 0 to less than 70 pbw of water.

13. The composition of claim 12, wherein composition comprises the one or more betaine surfactants.

14. The composition of claim 12, wherein composition comprises the one or more alkylpolyglucoside surfactants.

15. The composition of claim 12, wherein the composition comprises a mixture of the one or more betaine surfactants and the one or more alkylpolyglucoside surfactants.

16. The composition of claim 15, wherein the composition further comprises a polyhydric alcohol.

17. The composition of claim 12, wherein composition comprises one or more amine oxide surfactants.

18. A method for controlling a target plant, comprising diluting the pesticide composition of claim 12 with a diluent comprising water and applying the diluted pesticide composition to the target plant and/or the environment of the target plant.

* * * * *